US005335769A

United States Patent [19]

Klokkers-Bethke et al.

[11] Patent Number: 5,335,769

[45] Date of Patent: Aug. 9, 1994

[54] GLASS CONTAINER INTERNALLY COATED WITH A SILICONE AND HAVING AN IN SITU FREEZE-DRIED SOLID PRODUCT THEREIN, AND PROCESS OF MAKING THE SAME

[75] Inventors: Karin Klokkers-Bethke, Rödermark; Wilfried Fischer, Burscheid, both of Fed. Rep. of Germany

[73] Assignee: Schwartz Pharma AG, Monheim, Fed. Rep. of Germany

[21] Appl. No.: 972,076

[22] Filed: Nov. 5, 1992

Related U.S. Application Data

[63] Continuation of Ser. No. 693,925, Apr. 29, 1991.

[30] Foreign Application Priority Data

May 8, 1990 [DE] Fed. Rep. of Germany ....... 4014665

[51] Int. Cl.[5] .............................................. A61B 19/00

[52] U.S. Cl. .................................... 206/438; 428/34.7; 428/429; 560/121; 560/122; 562/503; 562/504

[58] Field of Search ...................... 428/34.6, 34.7, 428, 428/429; 215/DIG. 6; 560/121, 122; 562/503, 504; 34/5, 15, 92; 206/438

[56] References Cited

U.S. PATENT DOCUMENTS

| | | | |
|---|---|---|---|
| 2,504,482 | 4/1950 | Goldman | 604/403 |
| 3,654,926 | 4/1972 | Rietman | 604/416 |
| 3,717,498 | 2/1973 | Franz et al. | 117/70 A |
| 3,952,004 | 4/1976 | Monkhouse | 548/253 |
| 3,954,787 | 5/1976 | Monkhouse | 548/253 |
| 4,140,712 | 2/1979 | Hayashi et al. | 562/503 |
| 4,254,456 | 4/1981 | Ogle | 604/415 |
| 4,289,648 | 9/1981 | Hoskins et al. | 604/415 |
| 5,021,243 | 6/1991 | Becker et al. | 530/383 |

FOREIGN PATENT DOCUMENTS 702292 1/1954 United Kingdom .

OTHER PUBLICATIONS

"Hager's Manual of Pharmaceutical Practice", 4th Printing, vol. 7, Part A, p. 373; Springer Publisher, Berlin, Heidelberg, New York 1971.

National Formulary XIV, 1975, pp. 878–880.

Hartke, Mutschler, Publisher,"DAB 9 Commentary", vol. I, p. 353; Scientific Publishers GmbH, Stuttgart, Govi Publisher GmbH, Frankfurt, Aug., 1986.

H. Sucker, P. Fuchs, P. Speiser, "Pharmaceutical Technology", p. 762; George Thieme Publisher, Stuttgart Feb. 1978.

*Primary Examiner*—Ellis P. Robinson
*Assistant Examiner*—Michael A. Williamson
*Attorney, Agent, or Firm*—Marshall, O'Toole, Gerstein, Murray & Borun

[57] ABSTRACT

A freeze-drying process which reduces loss of the freeze-dried product comprising adding a liquid solution comprising a solid product dissolved in a solvent to a glass container having its inside surface coated with a silicone material; subjecting the container with the liquid solution therein to acceptable operable freeze-drying conditions to remove the solvent and leave the solid product in the container in the form of a dense compact coherent solid; and sealing the container to maintain the solid product stable over a useful storage shelf life.

An article of manufacture comprising a sealed glass container having its inside surface coated with a silicone material and containing an in situ freeze-dried dense compact coherent solid product.

5 Claims, No Drawings

GLASS CONTAINER INTERNALLY COATED WITH A SILICONE AND HAVING AN IN SITU FREEZE-DRIED SOLID PRODUCT THEREIN, AND PROCESS OF MAKING THE SAME

This application is a continuation of application Ser. No. 07/693,925, filed Apr. 29, 1991.

This invention relates to glass containers used as the primary packaging means for lyophilizates. More particularly, this invention is concerned with the in situ freeze-drying of a solution containing a solid product in a solvent, especially water, in glass containers having their inside surfaces coated with a silicone material.

BACKGROUND OF THE INVENTION

Moisture sensitive medicinal substances, which are to be administered parenterally, by infusion or injection, must be stabilized for storage. A customary stabilizing method is to dry a solution of the medicinal substance by removal of the solvent by lyophilization. For this purpose, aqueous solutions of the medicinal substances are placed in glass ampoules, glass vials, or glass bottles with puncturable caps, then frozen and freeze-dried under reduced pressure. Glass ampoules, after the drying is completed, are sealed off outside of the freeze-dryer by melting the glass shut. Vials and flasks with puncturable caps can be closed in the freeze-dryer with a freeze-dried previously mounted stopper.

Primarily important are the composition and concentration of the active substance in the solution, the type and manner of freezing, the respective temperature gradient used for the freeze-drying, as well as the final temperature, since they affect the pharmaceutical quality of the product. Furthermore, the temperature and pressure schedules, as well as the length of time used for the freeze-drying, the thickness of the solution layer to be freeze-dried, the geometry of the container with respect to the surface area in contact with the coolable and heatable container positioning plate, as well as moisture present during dealing or closure of the product, influence the pharmaceutical quality of the product.

Reliable feeding of a precise volume of solution to be dried into the container without the solution touching the ampoule neck or the vial rim, as well as the avoidance of circumstances which may lead to deposit of product residues at the neck or shoulder of the ampoules, or between the respective vial and stopper contact and sealing areas, are equally significant for maintaining a desired production output. Within the framework of being able to warrant the content of each individual vial, ampoule or bottle in a batch, and content uniformity from batch-to-batch, which contributes greatly to ensuring that the stated dosage can be withdrawn from the container, it is important to avoid risks such as which occurs when the freeze-dried solid product adheres to the vial rim and stopper sealing areas since that adversely affects product stability as a result of an inadequate seal.

The product residues at the neck of the ampoules are observable during sight inspection, which takes place when the product containers have been sealed or closed. Containers which fail the control inspection must be sorted out and removed. The lack of consistency and the shape of the product cake lead to a manufacturing loss or utilization loss where ampoules are concerned which, depending on raw material costs and manufacturing expenses, renders production variable and much more expensive. Product adherence between the sealing area of vials with their stoppers is not immediately visible during sight inspection control and is completely hidden after the protective caps are put on vials and glass bottles. This results in leakiness and permits uncontrolled passage of humid air into the vials during storage and, thus, there is a danger of hydrolytic decay of the active substances within the vials and bottles.

BRIEF DESCRIPTION OF THE INVENTION

It is an object of this invention to reduce or avoid the above described disadvantages, This object is achieved by using internally silicone coated glass containers in the manufacture of lyophilized products and particularly as the primary packaging containers for lyophilized products. By the term "primary packaging containers" is meant the container from which the product is removed by a customer or person administering the product. The term includes vials, ampoules and bottles.

DETAILED DESCRIPTION OF THE INVENTION

It has been known previously to use glass containers with silicone coated surfaces, as see "Glass Coating II" (Hartke, Mutschler, Publisher, DAB 9 Commentary, Volume I, page 353; Scientific Publishers GmbH, Stuttgart; Govi Publisher GmbH, Frankfurt, 1987). In accordance with the present state of the art, an internal silicone coating is used in glass injection bottles and injection ampoules to facilitate draining liquid residues from the container during the emptying process, which is particularly important when expensive materials, such as antibiotics, are in the containers. See Goldman U.S. Pat. No. 2,504,482 , U.K. patent 702,292 and H. Sucker, P. Fuchs, P. Speiser, Pharmaceutical Technology, page 762; Georg Thieme Publisher, Stuttgart 1978. Another prior art use of silicone coatings is to increase the hydrolytic resistance, but which use, however, is disputed among those skilled in the art (Hager's Manual of Pharmaceutical Practice, 4th Printing, Volume 7, Part A, page 373; Springer Publisher, Berlin, Heidelberg, New York 1971). Furthermore, silicone coatings have been used in syringes for reducing friction between the piston or a stopper (in the case of a two-chamber syringe) with the syringe cylinder. In regard to adsorption of active substances, e.g., peptides and proteins, into the glass container, treatment of the glass surfaces with silicones according to the prior art serves to reduce such adsorption into the glass. See Franz et al U.S. Pat. No. 3,717,498.

Even though there have been previous uses of silicone coated glass containers, one could not predict from such uses that lyophilizates produced in glass containers silicone coated inside would be improved to such an extent as to their compactness, coherence and form that a substantially faultless lyophilized product would be produced. Because the coherence, compactness and geometry of the freeze-dried solid product are improved so much, undesirable distribution of the solid product within the container in the areas of the shoulder and spear, or where a stopper contacts the surface of the container, is avoided.

Accordingly, a further development of this invention pertains to a method or process for preventing the loss of lyophilized product in that the product to be lyophilized is transferred to a primary or consumer packaging container made of glass which is coated on the inside surface with a silicone layer, after which it is lyophilized to form a compact product in a container to be dispensed to a user or consumer.

Upon freezing, an optimally formed body of ice of maximum density is obtained which can be considerably more evenly lyophilized than a layer of ice of varying thickness.

More specifically, according to one aspect of the invention a freeze-drying process is provided which reduces loss of the freeze-dried product comprising adding a liquid solution comprising a solid product dissolved in a solvent to a glass container having its inside surface coated with a silicone material; subjecting the container with the liquid solution therein to acceptable operable conditions of temperature and reduced pressure to remove the solvent by freeze-drying and leave the solid product in the container in the form of a dense compact coherent solid; and sealing the container by means which maintains the solid product stable over a useful storage shelf life.

The solid product can be a medicinal substance and the glass container can be a vial, ampoule or a glass bottle. The solvent can be water.

In a second aspect of the invention an article of manufacture is provided comprising a sealed glass container having its inside surface coated with a silicone material and containing an in situ freeze-dried dense compact coherent solid product. The glass container can be a vial, ampoule or bottle and the solid product can be a medicinal substance.

The lyophilization of a prostaglandin-$E_1$ product $PGE_1$, which contains $\alpha$-cyclodextrin and lactose besides $PGE_1$, using as a primary packaging means, a glass container made of Type I glass (That is, a glass particularly poor in sodium and which when in contact with aqueous solutions does not result in a pH change in the solutions. This is a glass classification defined in various pharmacopoeia, e.g., Ph., Eur. or USP XII; see also the National Formulary XIV, 1975, pages 878–880) will result in about a 10% loss of product during freeze-drying of the product in ampoules. This product loss is due to the product cake lacking coherence and having too little physical stability which leads to distribution of the lyophilizate throughout the entire container in about 10% of the ampoules of each batch. This product loss increases production costs when ampoules are used and, with the use of vials or bottles having puncturable caps, product storage stability is unpredictably reduced. Tests to reduce the product loss by modifying the freeze-drying conditions have been unsuccessful.

According to the invention it has been found surprisingly that coating the inside surface of a glass container with a silicone material substantially eliminates the above-mentioned manufacturing problems and product deficiencies.

The following example is presented to illustrate, but not limit, the invention.

EXAMPLE

Glass ampoules, made of Type I glass, are silicone coated on a Bausch & Stroebel washer-silicone coating machine with a spray method by using a 1% silicone emulsion formed by adding 550 ml of Baysilon H to 55 l of denatured water. Baysilon H is an aqueous emulsion of polydimethylsiloxane available from Bayer AG, Leverkusen, Germany.

The drying or solidification of the silicone coating takes place in a continuous oven wherein the holding time amounts to approximately 40 minutes at a temperature of about 300° C. The manufacturer of the silicone oil emulsion states in his directions for use of the product that a temperature of 330° C. is suitable with a shorter drying period and that temperatures up to 370°C. are not harmful if the drying period is further shortened. After drying, the silicone coated ampoules are washed three times with twice-distilled water at 50° C. followed by sterilization at a temperature of 300° C. for three minutes without the silicone coating being damaged.

A solution was made having a composition, per ampoule, of 20μg $PGE_1$ as an approximately 3% inclusion complex of the $\alpha$-cyclodextrin and 50 mg of lactose $H_2O$ in 400μl of water for injection purposes. This solution was filled, volumetrically in alternate 5 ml glass ampoules, made of glass Type I, or respectively 5 ml glass ampoules, made of glass Type I, with a silicone coating applied to the inside surface of the glass ampoules as described above.

Ampoules containing the $PGE_1$ solution were then subjected to a standard lyophilization process and to the same process with variations in freezing time and temperature and drying time. The standard lyophilization process is as follows:

1. A freezing chamber is loaded with the ampoules containing $PGE_1$ and the chamber is flooded with nitrogen.

2. Freezing

The initial temperature is about 25° C. to 30° C. Freezing of the ampoules under nitrogen down to −40° C. is completed in 7 to 8 hours. The freezing temperature is kept at −40° C. for another 27.5 to 30 hours.

3. Main Drying

The main drying is effected under nitrogen at −40° C. in 8 to 10 hours (minimum 8 hours). Subsequently, the ampoules are heated to +25° C. for 5 to 6 hours (minimum 5 hours). The temperature is then kept constant at +25° C. for at least another 6 hours. The vacuum used is $5\times10^{-2}$ mbar Wattage amounts to 12 KW.

4. Post-Drying

Final drying takes place under nitrogen at 25° C. for at least another 7 hours using a vacuum of $10^{-3}$ mbar. The ampoules are then removed from the chamber and sealed in the usual way by melting the ends of the ampoules. The results of the lyophilization process and variations therein are summarized in Table 1.

TABLE 1

Effect of Primary Packaging Means and Lyophilization Conditions On Product Quality

| Lyophilization parameter change with respect to standard manufacturing process | Ampoules - Type I glass | Ampoules - Type I glass; silicone coated inside |
|---|---|---|
| No Change | − | + |
| Shortened freezing time | − | + |
| Lengthened freezing time | − | + |
| Final freezing temperature lowered | − | + |
| Slower drying | − | + |
| Faster drying | − | + |

+ signifies a compact coherent lyophilizate cake of $PGE_1$
− signifies that the $PGE_1$ lacks coherence and that portions of $PGE_1$ lyophilizate were present at the ampoule spear and shoulders

What is claimed is:

1. An article of manufacture comprising:

a sealed glass container having its inside surface coated with a silicone material and containing an in situ freeze-dried dense compact coherent amount of solid prostaglandin-$E_1$.

2. An article of manufacture according to claim 1 in which the glass container is a vial, ampoule or bottle.

3. An article of manufacture comprising:

a sealed glass container having its inside surface coated with a silicone material and containing an in situ freeze-dried dense compact coherent amount of prostaglandin-E, selected from the group consisting of solid prostaglandin-$E_1$-alpha-cyclodextrin and a complex of prostaglandin-$E_1$-alpha-cyclodextrin and lactose.

4. An article of manufacture according to claim 3 in which the dense compact coherent solid is prostaglandin-$E_1$-alpha-cyclodextrin and lactose.

5. An article of manufacture according to claim 3, in which the glass container is a vial, ampoule or bottle.

* * * * *